United States Patent [19]
Flego et al.

[11] Patent Number: 5,903,211
[45] Date of Patent: *May 11, 1999

[54] MEDICAL TREATMENT DEVICE WITH A USER INTERFACE ADAPTED FOR HOME OR LIMITED CARE ENVIRONMENTS

[75] Inventors: Steven E. Flego, Portland; Mark E. Connell, Sandy, both of Oreg.

[73] Assignee: Althin Medical, Inc., Miami Lakes, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/796,971

[22] Filed: Feb. 7, 1997

[51] Int. Cl.$^6$ .................................................. G08B 13/02
[52] U.S. Cl. .................... 340/286.07; 340/573; 128/903; 128/904; 604/4; 604/29
[58] Field of Search .............................. 340/286.07, 573, 340/691; 128/903, 904, 897; 604/4, 29; 210/646; 455/67.7; 348/77, 553

[56] References Cited

U.S. PATENT DOCUMENTS

| | | |
|---|---|---|
| 3,946,159 | 3/1976 | Fay . |
| 3,986,498 | 10/1976 | Lewis . |
| 4,045,815 | 8/1977 | Griffith et al. . |
| 4,051,522 | 9/1977 | Healy et al. . |
| 4,838,275 | 6/1989 | Lee . |
| 4,883,462 | 11/1989 | Williamson et al. ..................... 604/53 |
| 4,885,795 | 12/1989 | Bunting et al. . |
| 5,207,621 | 5/1993 | Koch et al. ............................... 482/53 |
| 5,247,434 | 9/1993 | Peterson et al. . |
| 5,262,944 | 11/1993 | Weisner et al. . |
| 5,319,363 | 6/1994 | Welch et al. . |
| 5,412,419 | 5/1995 | Ziarati . |
| 5,434,611 | 7/1995 | Tamura . |
| 5,441,047 | 8/1995 | David et al. . |
| 5,527,239 | 6/1996 | Abbondanza ............................... 482/8 |
| 5,545,130 | 8/1996 | Hofmann et al. ........................... 604/4 |
| 5,567,320 | 10/1996 | Goux et al. ................................. 604/4 |

*Primary Examiner*—Thomas J. Mullen, Jr.
*Assistant Examiner*—Julie Lieu
*Attorney, Agent, or Firm*—Klarquist Sparkman Campbell Leigh & Whinston, LLP

[57] ABSTRACT

A medical treatment device is disclosed that utilizes an entertainment displays such as a standard television set, to control the medical treatment device. For example, alarm conditions may be displayed and a user (such as a patient) can respond to such alarm conditions. During an uneventful treatment, the patient can view programs (e.g., television programs) on the entertainment display. The medical treatment device can override the entertainment program and cause the entertainment display to display information related to operation or status of the medical treatment device. The medical treatment device can also include a user input (e.g., keyboard, mouse, joystick, etc.) allowing the patient to move a selector image being displayed by the entertainment display to enable the patient to control the medical treatment device.

31 Claims, 6 Drawing Sheets

MEDICAL TREATMENT DEVICE WITH A USER INTERFACE ADAPTED FOR HOME OR LIMITED CARE ENVIRONMENTS

FIELD OF THE INVENTION

This invention relates generally to medical apparatus operable to perform an extracorporeal blood treatment using a hemodialyzer, hemofilter, hemodiafilter, or analogous blood-processing device. More particularly, the invention relates to controlling such apparatus through a readily visible, accessible and low-cost user interface.

BACKGROUND OF THE INVENTION

Patients requiring ongoing periodic extracorporeal blood treatment have traditionally received their treatments at clinics or similar locations staffed by skilled nurses and technicians who administer the treatments and operate the apparatus (i.e., the machines) used to perform the treatments. Should a treatment alarm condition arise during treatment, indicating a potentially unsafe condition for the patient being treated, the machine typically produces an alarm response that is usually both audible and visual. (The visual aspect of the alarm usually includes some indication of the type and/or source of the alarm condition). When an alarm condition occurs, the clinic staff are trained to respond by determining the cause of the alarm and taking corrective action.

Many patients undergoing periodic extracorporeal blood treatments find having to receive their treatments in a clinic very inconvenient as well as expensive. This has long been recognized and efforts have been ongoing to make it possible for increasingly more patients to perform their treatments at home. Whereas some "home" patients engage a helper to assist with the treatments as required, others fend for themselves. Virtually all "home" patients have a treatment apparatus that remains in the patient's home all the time. The "home" patient has usually received at least some training in how to administer their own treatment as well as operating and maintaining the apparatus. The training usually includes responding to and correcting alarm conditions.

Extracorporeal blood treatments tend to require long periods of time per treatment. For example, a typical skillfully administered hemodialysis treatment requires about four hours including setup and end-of-treatment tasks. Patients undergoing such treatments usually sit in a comfortable chair or upright in bed, and often occupy such time by watching television, reading, or simply dozing.

Patients having to endure periodic extracorporeal blood treatments, such as maintenance hemodialysis, usually have poorer health, mainly due to their disease, than persons in the general population. As a result, such patients tend to be sedentary and many have impaired mobility and/or flexibility. Also, the nature of the treatment requires that the patient remain quiescent during treatment. This is because the patient, during treatment, is connected usually to two extracorporeal blood conduits that conduct the patient's blood extracorporeally to a blood-processing device (such as a hemodialyzer) mounted on the apparatus, and from the blood-processing device back to the patient. Connection of the blood conduits to the patient is usually done by needle or cannula to a suitable blood access in the patient. The blood-processing device is hydraulically connected to the treatment apparatus.

During treatment, whether in the home or in a clinic, the apparatus is usually situated behind or beside the patient. Such an arrangement is normally preferred to keep the length of the extracorporeal blood conduits as short as practicable, and because having the apparatus in direct view is discomforting for many patients. Locating the apparatus behind or beside the patient also allows the patient to view an entertainment display, such as a television set, during treatment. Allowing a patient to be entertained during treatment relieves stress and focuses the patient's attention on something other than the treatment.

Hence, even though the treatment apparatus normally includes some form of user interface, such as a display screen, to allow the patient or other user to control various treatment parameters and respond to alarm conditions, the patient is normally not facing the apparatus. This causes two problems: Firstly, the patient may have difficulty seeing the apparatus. Displays on the apparatus can be difficult for the patient to see, particularly if the patient is lying in bed. Secondly, many patients are elderly and/or have limited physical capacity to reach for the apparatus when required. For example, since some alarms tend to be "nuisance" alarms, it would be advantageous for such patients, especially when performing their treatments at home, to know whether or not an alarm is a nuisance alarm before having to get up and take corrective action.

U.S. Pat. No. 4,051,522 to Healy et al. discloses a television system operable to allow persons, usually clinical personnel, to passively view patient data on a television distribution system. Whereas an apparatus according to Healy et al. makes it easy for a person to view information related to the apparatus, the Healy et al. apparatus is not readily adaptable to the home or other limited-care environments. For example, the Healy et al. apparatus does not alert a patient or other user to an alarm condition, nor does the Healy et al. apparatus allow a patient or other person to change treatment parameters.

In view of the foregoing, there is a need for an apparatus for performing medical treatments of blood extracorporeally circulated from a patient, wherein the apparatus is operable to alert a home patient or a patient in some other limited-care environment of specific alarm conditions as they occur, and that can readily provide information to the patient about the specific alarm condition without the patient having to exert a substantial effort to look at the apparatus and/or take corrective action.

There is also a need for such an apparatus that allows a patient to control the apparatus through a readily visible, easily accessible, and easy-to-use user interface.

There is also a need for such an apparatus that can fulfill the foregoing needs without adding substantial cost.

SUMMARY OF THE INVENTION

The foregoing needs are fulfilled by the present invention that provides, inter alia, an extracorporeal blood-treatment system comprising in combination a medical treatment device and an entertainment display. The medical treatment device performs the actual extracorporeal blood treatment of a patient and can be placed outside the patient's view during treatment. The entertainment display, which can be a standard television set, is operable to entertain the patient during the treatment and to contemporaneously provide, if needed or desired, the patient with information concerning the medical treatment device (e.g., information relating to an alarm condition). Thus, for example, the extracorporeal blood-treatment system allows the patient to view a normal television program whenever the medical treatment device is operating properly, but to automatically interrupt the program with a display of certain device-related information whenever an alarm condition arises or at other times as required or desired. The patient is entertained during the treatment, but can also be contemporaneously informed as to the operational status of the medical treatment device, without the patient having to shift positions in the chair or bed on which the patient is resting during treatment.

According to another aspect of the invention, an extracorporeal blood-treatment system according to the present invention preferably also allows the patient to control the medical treatment device using the entertainment display and a user input device (e.g., keyboard, mouse, joystick, or the like). The patient can move a selector image or pointer on the entertainment display for changing treatment parameters or for obtaining further information about an alarm condition.

In the case of an alarm condition, after the alarm condition is corrected, the medical treatment device can be operable to override the display of information related to the alarm condition and resume display of the previously overridden entertainment program.

In yet another aspect of the invention, multiple medical treatment devices may be monitored from a single display. A single input device may also be used to control any of the medical treatment devices.

Since the information relating to the medical treatment device is presented on an entertainment display normally viewed by the patient for entertainment during the treatment, the patient can have ready access to such information even when the medical treatment device is not within the patient's view. Furthermore, by manipulating the user input, the patient can control the medical treatment device without changing position and without having to reach for the medical treatment device. The patient also has the flexibility of using an entertainment display of any size. For example, a patient with poor vision can utilize a large television set as an entertainment display so that information, such as alarm conditions, are easier to read.

The foregoing and other advantages and features of the invention will be apparent from the following detailed description, which proceeds with reference to the following drawings.

DETAILED DESCRIPTION OF A PREFERRED EMBODIMENT

Figure 1:
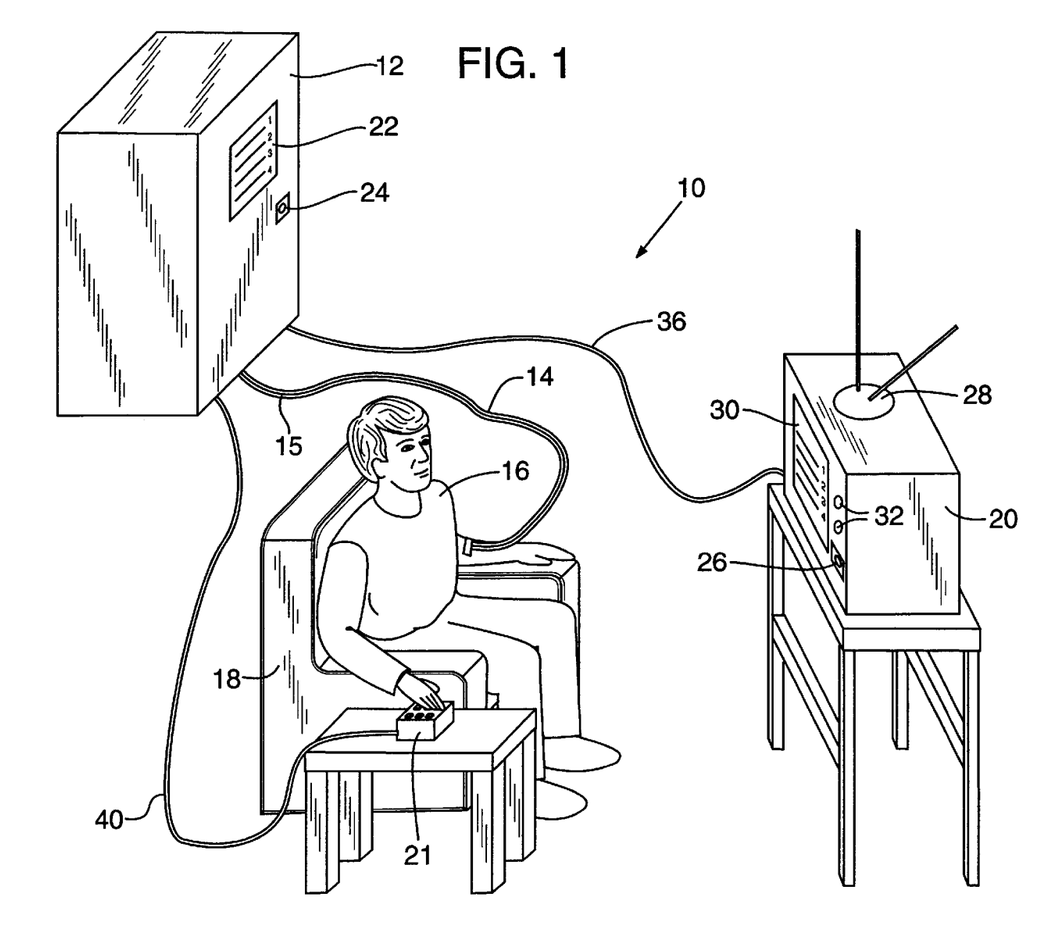
FIG. 1 is a perspective view of an extracorporeal blood-treatment system according to the invention connected to a patient; specifically, the patient is being treated by a medical treatment device while the patient watches an entertainment display (in this instance a television set) and information concerning the treatment device is being displayed on the entertainment display which is connected to the medical treatment device.
Figure 2:
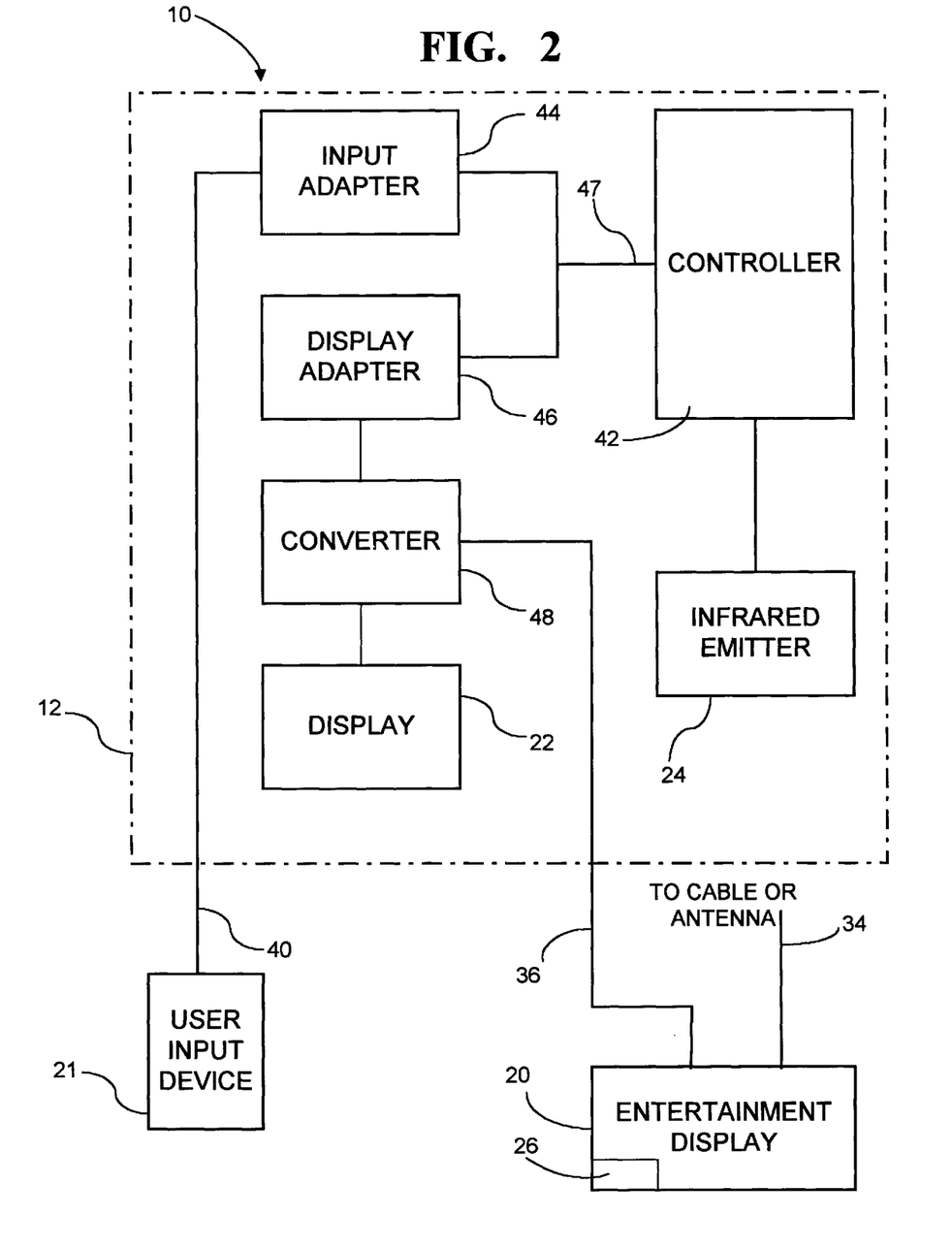
FIG. 2 is a schematic diagram of the extracorporeal blood-treatment system of FIG. 1.

Referring to FIGS. 1 and 2, an extracorporeal blood-treatment system 10 according to the present invention comprises, inter alia, a medical treatment device 12 and an entertainment display 20. Extracorporeal blood conduits 14, 15 are connected to the medical treatment device 12. The extracorporeal blood conduits 14, 15 route blood from a patient 16 for treatment by the medical treatment device 12, and return treated blood to the patient 16. As the patient's treatment progresses, the patient 16 rests, for examples in a chair 18 while watching the entertainment display 20.

The entertainment display 20 can be a standard television set (as shown) or computer display separate from any display on the medical treatment device 12. The entertainment display 20 is connected to the medical treatment device 12 via a cable 36 or other suitable manner. The entertainment display 20 is operable to provide information to the patient concerning the medical treatment device 12. For example, if an alarm condition should arise during the course of the patient's treatment, the medical treatment device 12 triggers the entertainment display 20 to interrupt the entertainment program the patient is watching so as to display information relating to the alarm condition. A user input 21 electrically connected to the medical treatment device 12 allows the patient 16, while continuing to watch the entertainment display 20, to obtain further information concerning the alarm condition, and to take corrective action.

A patient also can control operation of the medical treatment device 12 whenever an alarm condition does not exist. For example, if the patient is cold, he may wish to increase the temperature (over a limited range) of the medical fluid (such as dialysate) used to treat the patient's extracorporeal blood. In such a case, the patient can switch the entertainment display 20 to display information related to the medical treatment device 12. The patient can then manipulate the user input device 21 to change information on the medical treatment device using the entertainment display as a visual interface.

The medical treatment device 12 can be, for example, a hemodialysis machine, wherein extracorporeal blood conducted in the conduit 14 is urged by the medical treatment device 12 to pass through a hemodialyzer (not shown, but conventionally understood to be mounted to the medical treatment device 12) for treatment, and treated blood conducted through the conduit 15 is urged by the medical treatment device 12 to return to the patient 16.

The medical treatment device 12 further comprises a dedicated display 22, such as (but not limited to) a CRT or an LCD, for displaying information related to the operation of the medical treatment device. An exemplary medical treatment device possessing such a display in the form of a CRT "touch screen" is disclosed U.S. Pat. No. 5,247,434 to Peterson et al. (the '434 patent), which is incorporated herein by reference.

The medical treatment device 12 also comprises an infrared emitter 24 or other suitable signal-transmitting component used to send a signal as required from the medical treatment device 12 to the entertainment display 20. The entertainment display 20 comprises a conventional infrared receiver 26 or other suitable signal-receiving component sensitive to and operable to receive the signal from the emitter 24. Upon receipt of the signal by the receiver 26, the entertainment display 20 is caused to switch from displaying an entertainment program to displaying information concerning the medical treatment device.

The receiver 26 is the same as is found on virtually all conventional television receivers capable of being used with a hand-held remote control. Thus, the receiver 26 is operable to receive signals from a remote control (not shown, but also conventionally understood to include an infrared emitter) causing the entertainment display 20 to change channels or adjust the sound volume, for example. In other words, the emitter 24 and receiver 26 are standard components used in conjunction with contemporary remote-control television sets and are well known in the art.

An antenna 28 can be connected to the entertainment display 20 for receiving radio frequency (RF) broadcast signals to display broadcast television programs on a viewing "screen" 30 (typically a CRT screen) of the entertainment display 20. Alternatively, a standard television cable can be used to supply the RF signals to the entertainment display 20, as in the case of cable television. In either case, the antenna or cable is typically connected to an input terminal, usually located on a rear of the entertainment display 20, designated as a VHF/UHF input terminal. Control knobs 32 allow manual adjustment of channels and/or the viewing screen 30.

The medical treatment device 12 and the entertainment display 20 are preferably connected together via a signal conductor 36, such as a coaxial cable. The signal conductor 36 is used to conduct video signals from the medical treatment device 12 to the entertainment display 20 whenever, for example, an alarm condition arises. Referring to FIG. 2, the signal conductor 36 is coupled directly to the entertainment display 20 through a video input (not shown). The entertainment display can be switched from displaying RF signals received through the VHF/UHF input terminal to displaying video signals received through the video input.

Thus, the medical treatment device 12 cooperates with the entertainment display 20 to present information pertaining to the medical treatment device to the patient 16. For example, whenever an alarm condition occurs, the medical treatment device 12 emits a modulated infrared command signal from the infrared emitter 24. The command signal propagates toward and is received by the infrared receiver 26 on the entertainment display 20. Upon receiving the command signal, the entertainment display 20 changes from receiving RF signals from the antenna 28 to receiving video signals from the medical treatment device.

When switched to display video signals, the entertainment display displays signals received through the signal conductor 36, rather than cable or antenna signals received on the signal path 34. For example, as illustrated in FIG. 1, information pertaining to the medical treatment device is being presented to the patient 16 as can be seen by the identical images displayed on the screen 30 of the entertainment display 20 and the display 22 of the medical treatment device 12.

The user input device 21 is connected to the medical treatment device 12 through an input-device conductor 40. The user input device 21 can be any of various input devices well-known in the art, such as a joy stick, track ball, mouse, keyboard, glide point, or any analogous pointing device, or any modification or combination of these devices. The user input device 21 allows the patient 16 to move a selector image or pointer on the viewing screen 30, whenever the viewing screen is displaying information from the medical treatment device. Thus, a user can, for example, ascertain the cause of an alarm condition and control and adjust treatment parameters of the medical treatment device 12 in an effort to rectify the alarm condition. Whereas the user input device 21 can be a full keyboard, a full set of keys including alphanumeric keys, function keys, and control arrows is usually unnecessary. Rather, the keyboard need only comprise a subset of a full set of keys, such as control-arrow keys and one or more special-function keys so that the patient 16 can, for example, move a selector image on the display 30 in any of various desired directions and browse through an hierarchical graphical menu.

As is well-known in the art of keyboards and related devices, the user input device 21 typically comprises a keyboard controller circuit (usually on one or more integrated circuits or "chips") to receive signals from individual keys and deliver corresponding signals in a computer-readable format indicating which key was pressed. Examples of suitable keyboard-controller chips include the PIC16C56-XT and PIC16C57-XT manufactured by Microchip, Inc.

As mentioned above, the user input 21 can include special-function keys. Examples of special-function keys include a "mute" key for disabling an audible alarm or a "reset" key for resetting the medical treatment device 12 after an alarm condition has been corrected. These keys are preferably located on the user input 21 and may be "clicked" or pressed to implement the desired function.

Alternatively, special functions can be implemented through a hierarchical graphical menu displayed on the viewing screen 30. Examples of display formats used in a graphical menu system are disclosed in the 434 patent referenced above. Using such a menu system, the patient 16 can set alarm limits, engage special functions, and control other parameters in the medical treatment device 12.

FIG. 2 provides a block diagram of major relevant components of the extracorporeal blood-treatment system 10. A medical treatment device 12 according to the present invention is enclosed within dashed lines and includes a controller 42, an input adapter 44, a display adapter 46, a converter 48, the dedicated display 22, and the infrared emitter 24 (or analogous signal-conducting means). An example of a controller 42 is an embedded PC-based computer system similar to the one disclosed in the '434 patent. As is well understood in the art, the controller 42 includes a PC-based "mother board" (not shown) that allows different adapter "cards" to be plugged therein and controlled through a system bus 47. By way of example, the currently preferred embodiment of the controller 42 employs a 80386 microprocessor manufactured by Intel Corp., but any of various microprocessors can be used, such as (but not limited to) any processor in the 80X86 family of Intel microprocessors or compatible processors.

The input adapter 44 is a standard input/output (I/O) adapter provided on a circuit board ("card"), such as manufactured by Data Technology Inc. or Diamond Flower, Inc. The display adapter 46 is a standard monitor card, such as manufactured by ATI Technology, Number Nine Computer, or Diamond Multimedia Systems, Inc. Thus, the adapters 44, 46 are well known commercially available cards that can be plugged into the system bus 47 on the mother board of the controller 42.

The input adapter 44 is connected to the user input device 21 through the input conductor 40. The input adapter 44 is operable to receive control signals from the user input device 21 and to format and transfer such control signals to the controller 42 for interpretation.

The display adapter 46 and converter 48 are operable to electronically interpret image-generating signals for display on the dedicated display 22 and on the entertainment display 20. More specifically, the display adapter 46 receives signals from the controller 42 via the system bus 47, and converts the signals for retransmission in VGA format. The converter 48 is a VGA-to-video converter that retransmits the VGA signals to the dedicated display 22. The converter 48 also transmits video signals corresponding to the VGA signals received from the display adapter 46, but converted into video format for the entertainment display 20. Such converters are well known in the art and are commercially available, such as a converter named "Pro PC" and manufactured by AITech. The video signals transmitted to the entertainment display 20 can be in NTSC standard, PAL standard, or SECAM standard used in the United States, Europe and South America, respectively. The system can easily be adapted to accommodate other standards or new standards that are developed by removing the existing converter 48 and replacing with a different converter adapted to supply the different or new standard.

Signals from the converter 48 are conducted to the entertainment display 20 via the signal conductor 36. The entertainment display 20 has two modes of operation. In a first mode, images are displayed on the viewing screen 30 that correspond to incoming RF signals from the antenna 28 or cable 34. In a second mode, images displayed on the viewing screen 30 correspond to video signals received via the signal conductor 36 from the medical treatment device 12. The second mode of operation is implemented whenever the entertainment display 20 is switched to display video signals through the video input on the entertainment display. The first mode of operation is implemented whenever the entertainment display 20 is set to receive and display RF signals. Such modes of operation are common when a standard television set is used with, for example, a video cassette recorder (VCR) wherein a user can watch standard broadcast or cable-routed television programs on different television channels in the first mode of operation, but can switch to a video input to view a VCR tape in the second mode of operation.

Older television sets switch between viewing RF signals and video signals by changing channels. For examples signals from a video input are displayed when the channel is changed to a predetermined channel (channel 3 on most televisions). When any other channel is viewed, the television displays images associated with RF signals.

Continuing further with FIG. 2, the controller 42 is connected to the infrared emitter 24 to allow the medical treatment device 12 to command a switch on the entertainment display 20 from viewing television programs for entertainment to video information concerning the medical treatment device. In other words, the medical treatment device 12 is operable to automatically switch the entertainment display 20 from the first mode of operation to the second mode of operation. Thus, in the second mode of operation, the medical treatment device 12 interacts with the entertainment display 20 in a manner similar to that of a VCR in that the medical treatment device 12 provides video signals (e.g., corresponding to an alarm condition) to the entertainment display 20. In the second mode of operation, the viewing screen 30 displays images and information related to the medical treatment device to the patient 16 without the patient having to make any effort to see the medical treatment device 12.

Figure 3:
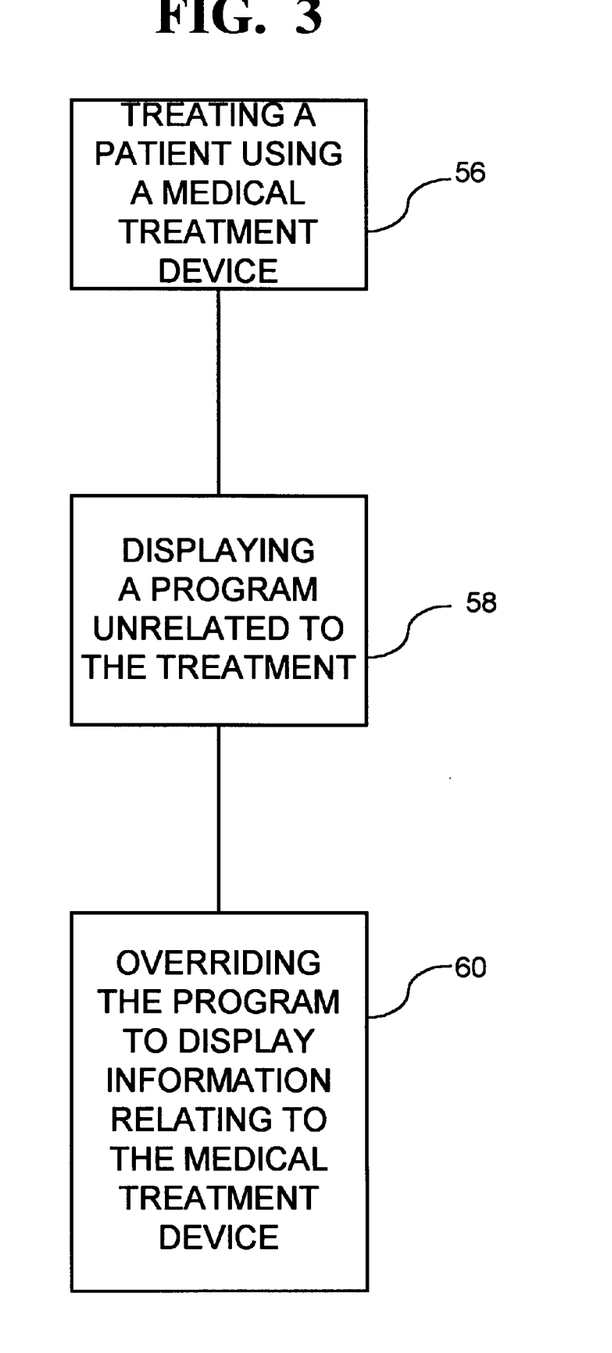
FIG. 3 is a flow chart showing steps performed by a preferred embodiment of the extracorporeal blood-treatment system for displaying information to a user.
Figure 4:
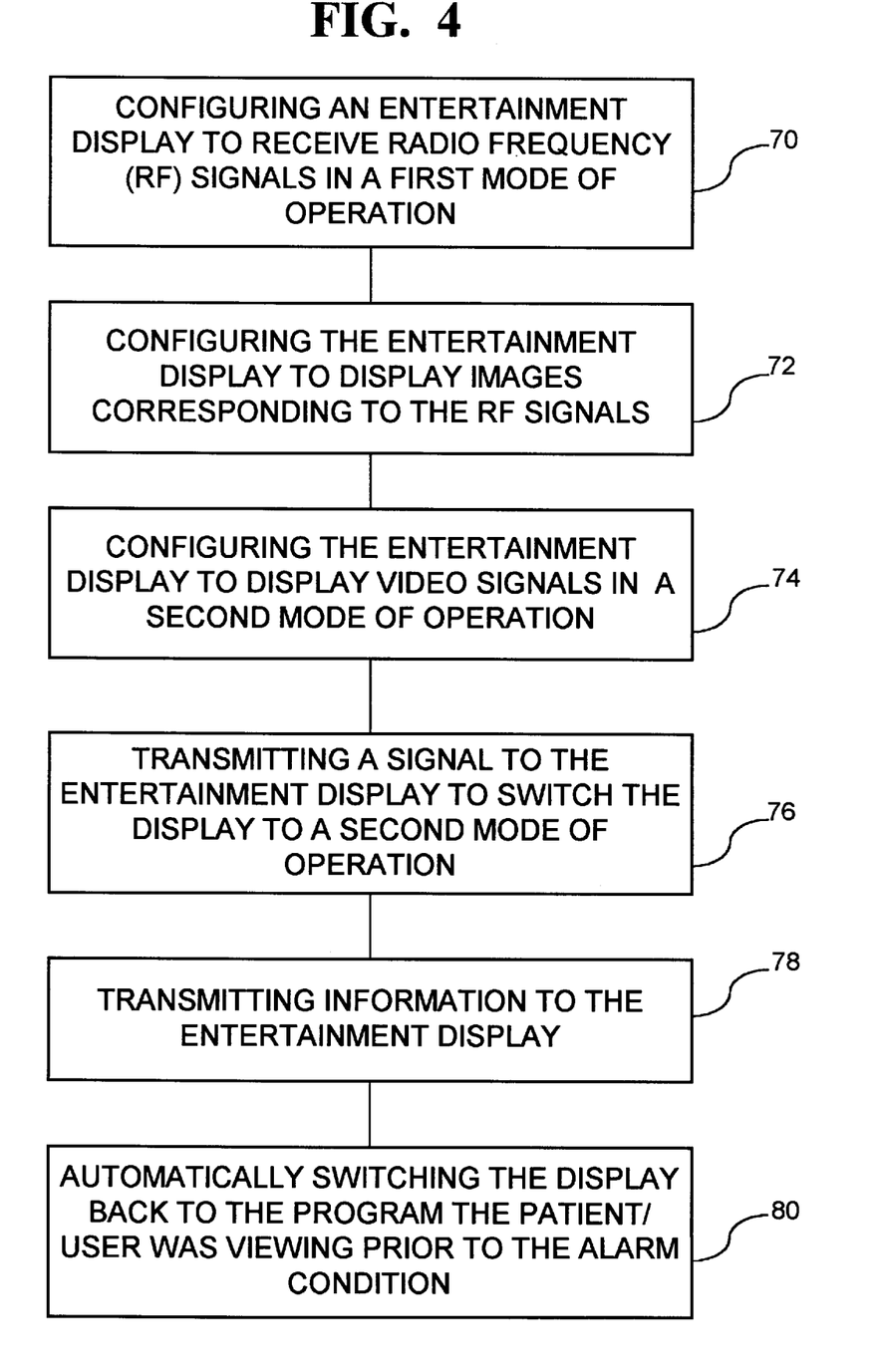
FIG. 4 is a more detailed flowchart showing steps performed by a preferred embodiment of the extracorporeal blood-treatment system in displaying information to a user.
Figure 5:
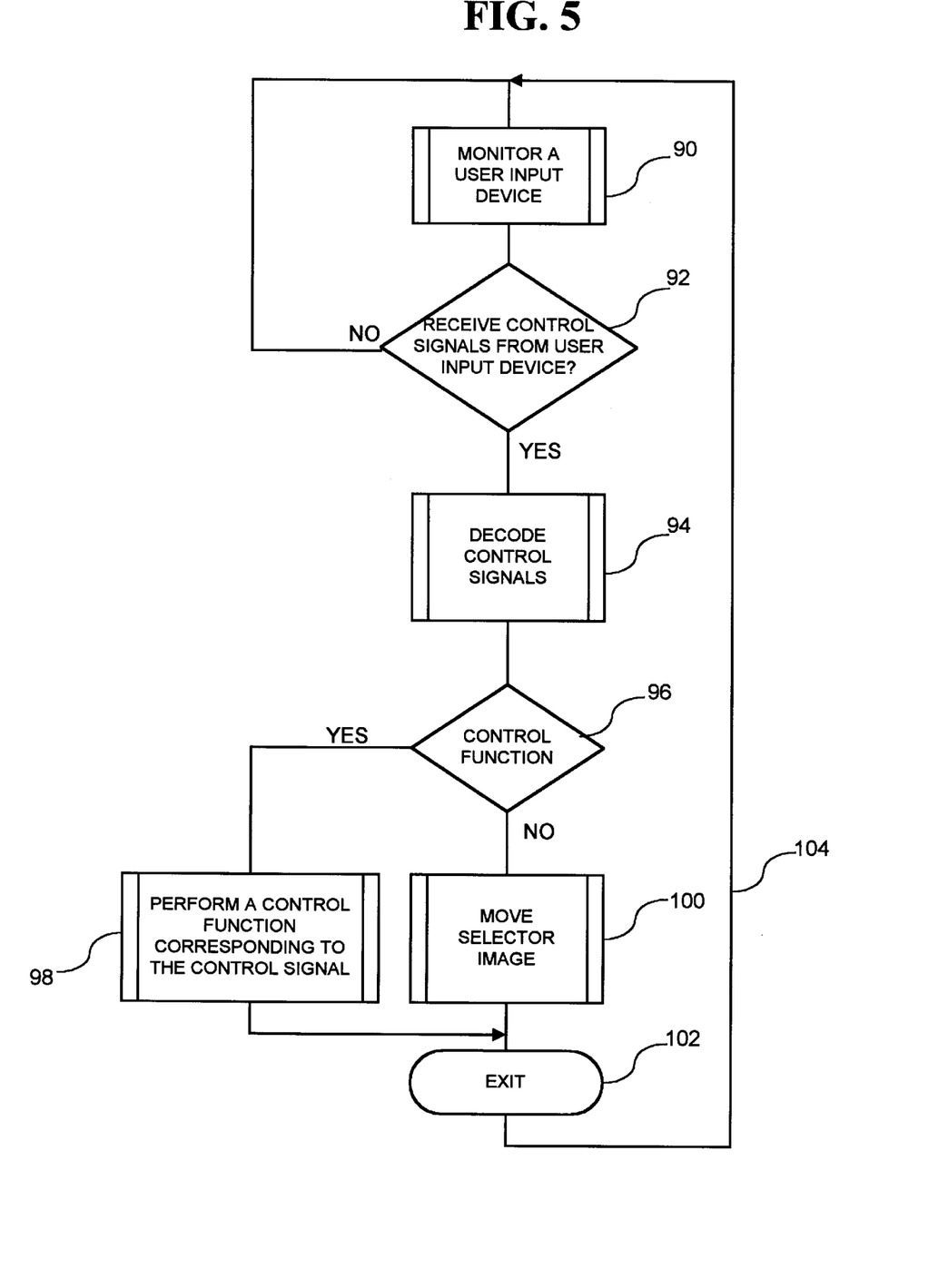
FIG. 5 is a flow chart showing steps, performed by a preferred embodiment of the medical treatment device, for receiving input from a user input device so that the patient can control the medical treatment device while watching the entertainment display.

Further details of the extracorporeal blood-treatment system 10 are illustrated in FIGS. 3, 4, and 5, wherein illustrated steps are run by software routines in the controller 42. Referring first to FIG. 3, step 56 pertains to treating a patient using the medical treatment device 12 while the medical treatment device 12 monitors various parameters of the treatment to ensure patient safety. For example, in the case of hemodialysis, the medical treatment device 12 ensures, inter alia, that the patients extracorporeal arterial and venous pressure values are within acceptable and safe limits (and triggers an alarm if the limits are exceeded). Additionally, the medical treatment device 12 can monitor for air in the extracorporeal blood conduit returning blood to the patient (and trigger an alarm if a significant amount of air is detected). Details on these aspects are set forth, for example, in the previously cited '434 patent.

In step 58, the viewing screen 30 displays programs unrelated to and independent of the medical treatment device 12 so that the patient is entertained during treatment. For example, in step 58, the viewing screen 30 displays standard broadcast or cable television programs.

It is noted that the entertainment display 20 need not be a television set. Rather, for example, a patient may wish to work using, or be entertained by, a computer during treatment. In such a case, the program being displayed by the viewing screen 30 is generated by a computer program, and the signals received by the entertainment display 20 are computer signals. Whether the entertainment display 20 is a television set or a computer, or some other type of entertainment display, the patient 16 can view while being treated entertaining images unrelated to the medical treatment device 12 or its functioning.

In step 60, the medical treatment device 12 overrides the program displayed in step 58 and causes the viewing screen 30 to display instead appropriate information related to the medical treatment device. Thus, for example, the patient may be automatically visually and, preferably, audibly alerted to the existence of the alarm condition, and is presented with information helpful for determining the cause of the alarm. Because the entertainment display 20 is preferably situated for easy viewing by the patient 16, and because the viewing screen 30 is normally the focus of the patient's attention as treatment progresses, the patient is immediately and reliably alerted to the alarm condition.

FIG. 4 is a flowchart showing the displaying and overriding steps 58, 60, respectively, of FIG. 3 in greater detail. In steps 70 and 72, an alarm is not pending and the entertainment display 20 is configured to receive, and actually does receive, RF signals from a cable or antenna. Consequently, the viewing screen 30 displays images corresponding to the RF signals. According to the first mode of operation as discussed above, the entertainment display 20 can display images from any of a number of channels provided by the antenna or cable.

In step 74, the entertainment display 20 is configured to display video signals in the second mode of operation. For example, most television sets can switch to a video mode through which the television can display images corresponding to video signals, rather than RF signals.

In step 76, the controller 42 switches the entertainment display to the second mode of operation. For example, if the patient's extracorporeal arterial or venous blood pressure rises or falls outside preset safety limits, or if air is present in the extracorporeal venous blood conduit, the medical treatment device 12 produces an alarm response. The controller 42, upon detecting such an alarm condition, transmits a signal via the infrared emitter 24 that commands the entertainment display 20 to switch from the first mode of operation to the second mode of operation. The command signal is received by the infrared receiver 26 on the entertainment display 20. Upon receiving the command signal, the entertainment display 20 switches from whatever channel the patient is currently watching to the video input in which the viewing screen 30 begins displaying information provided by the medical treatment device 12 via the signal conductor 36. Thus, the previously displayed entertainment program is automatically overridden so as to be no longer displayed and information related to the medical treatment device 12 is displayed instead by the entertainment display 20.

In step 78, the medical treatment device 12 transmits information, via the signal conductor 36, to the entertainment display 20. Such information can include any of various treatment parameters such as extracorporeal blood-flow rate, extracorporeal arterial or venous pressure, or the presence of air in the extracorporeal venous blood line.

Step 80 is optional. In step 80, the medical treatment device 12 automatically switches, upon rectification of an alarm condition, the entertainment display 20 back to the program the patient was originally viewing prior to the onset of the alarm. This feature can be implemented by switching the television set back to the first mode of operation.

The steps shown in FIGS. 3 and 4 also apply when no alarm condition exists and the user merely wishes to change treatment parameters in the medical treatment device.

The extracorporeal blood-treatment system 10 can also receive patient input concerning the treatment from the user input device 21. FIG. 5 shows representative steps taken by the extracorporeal blood-treatment system 10 for receiving patient input whenever the entertainment display 20 is in the second mode of operation. In step 90, the medical treatment device 12 monitors the user input device 21 to determine if the patient is attempting to exert control, via the user input device 21, over operation of the medical treatment device 12. Such monitoring of the user input device 21 is performed by the controller 42 which receives control signals from the user input device 21 through the input adapter 44.

The controller 42 can detect signals from the user input device 21 in a number of ways. For example, the controller 42 can have software-generated interrupts that are activated upon receiving a signal from the user input device 21; alternatively, the controller 42 can be provided with a software loop in which the controller periodically checks for user input. In either event, the controller 42 receives control signals from the user input device 21 as illustrated in step 92. By such control signals, the patient can, for example, move a selector image displayed on the viewing screen 30 or select an element or parameter to which the selector image points or to provide a special-function key located on the user input device 21.

In the case of special-function keys, the entertainment display 20 need not be in the second mode of operation to control the medical treatment device 12. An example of a special-function key is a "mute" key that will turn an alarm off without the entertainment display 20 being in the second mode of operation.

In step 94, the controller 42 decodes the control signals from the user input device 21. Such decoding can be accomplished by any of various different software techniques. For example, if only a limited number of possible input control signals exist, a SWITCH/CASE-type statement can be used to compare input control signals to predetermined values of such signals. Once a control signal matches a predetermined value thereof, further action may be taken.

In the case where a larger number of input control signals are used, a lookup table can be used by the controller 42 to decode the input control signals. Other software techniques for decoding control signals can be used as are well known in the art.

In step 96, the decoded control signal is checked to determine whether or not it is an actual control function. Control functions are used to change the value of parameters on the medical treatment device 12, to advance the patient through a series of hierarchical graphical menus, or to implement predetermined functions via the special-function keys on the user input device 21. If the control signal is a control function, the process of FIG. 5 advances to step 98. If the control signal is not a control function, the process advances to step 100.

In step 98, the controller 42 performs the control function provided by the user input device 21. One possible control function is to advance the patient through an hierarchical graphical menu displayed on the viewing screen 30. For example, the patient can move a selector image on the viewing screen 30 to a desired menu item; a proper control signal (e.g., depressing an "enter" key or the clicking of a mouse button) results in the display on the viewing screen 30 of a submenu item corresponding to the menu item. The patient can also respond to and correct an alarm condition in such a manner. For example, the patient can select a treatment parameter that is outside a predetermined limit and change the parameter appropriately to move the parameters within the limit.

Thus, the extracorporeal blood treatment system 10 allows a patient or other user to selectively control operation of the medical treatment device 12 by changing desired treatment parameters or by browsing through an hierarchical graphical menu as displayed on the viewing screen 30. Examples of different displays and operations that can be carried out are disclosed in the '434 patent cited above.

If a control function is not indicated in step 96, then step 100 is executed. In this case, a selector image on the viewing screen 30 moves in a direction corresponding to the input signal. Moving a selector image is typically a precursor to receiving a control function input from the patient. For example, a patient can move the selector image on the viewing screen 30 to a main menu item or to a desired parameter and then depress a control function key to obtain further information about the main menu item or to change the desired parameter. The selector image can be a box outlining different selectable control keys on the viewing screen 30 so that a move-selector image command automatically moves the box to an adjacent selectable control key. The selector image can alternatively be a pointer arrow movable to any desired location on the viewing screen 30, as is typically used in "windows" applications programs utilizing a mouse or glide-point input device.

After either step 98 or 100, the process shown in FIG. 5 exits at step 102 and returns to the monitoring step 90 as indicated by the arrow 104.

Figure 6:
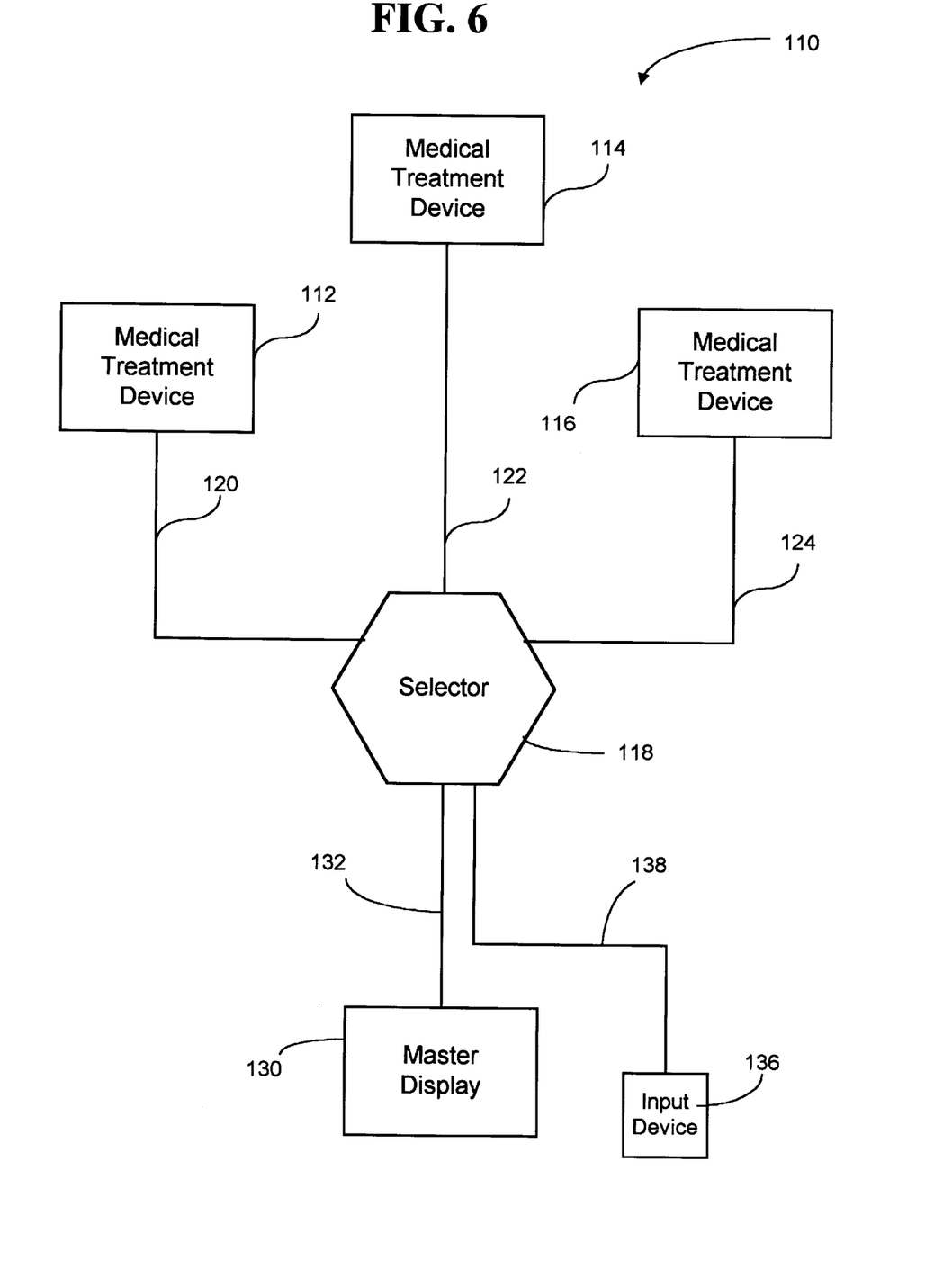
FIG. 6 is a block diagram of a system, according to another aspect of the invention, wherein multiple medical treatment devices can be monitored and controlled using a master display.

FIG. 6 shows a block diagram of another aspect of the invention wherein an extracorporeal blood-treatment system 110 is used to treat multiple patients in a limited-care environment. The system 110 includes a plurality of medical treatment devices 112, 114, and 116. Although three medical treatment devices are shown, any number of medical treatment devices can be used in the system 110. The medical treatment devices 112, 114, and 116 are coupled to a selector 118 through cables 120, 122, and 124, respectively. The selector is coupled to a master display 130 through a cable 132. An input device 136 is also coupled to the selector by a cable 138. The input device 136 is similar to the input device 21 (FIG. 1) described above.

A user can use the master display to display information relating to any of the medical treatment devices 112, 114, and 116. The input device 136 allows the user to control one or more of the medical treatment devices. The system 110, thus, provides an environment whereby one person can monitor multiple patients and medical treatment devices and control the medical treatment devices (e.g., change treatment parameters) from a single location.

The selector 118 receives signals to be displayed on the master display 130 from cables 120, 122, and 124. The selector is switching hardware that controls which of the signals on cables 120, 122 and 124 pass through to cable 132 for display on master display 130. In the case where a single medical treatment device is displayed, the master display provides a full-screen display for that medical treatment device.

The selector may also provide additional functionality whereby display signals from multiple treatment devices are transmitted over cable 132. In such a case, the master display may segment a display screen into portions. The master display can, consequently, display information related to multiple treatment devices simultaneously.

The cables 120, 122, and 124, each contain a display conductor for supplying display signals to the master display, as already described, and an input signal conductor for transmitting input signals received by the selector 118 through cable 138. Based on the current medical treatment device selected, signals on conductor 138 are routed to the appropriate input signal conductor for the selected medical treatment device.

The selector 118 may be switched to a particular medical treatment device by the input device 136 or by the medical treatment devices. For example, if a user wishes to control a particular medical treatment device, the user may use the input device to switch the selector 118 to the desired medical treatment device.

A medical treatment device may also switch the selector in the event of an alarm condition. For example, in the event of an alarm, a medical treatment device may send an infrared signal transmitted by an infrared emitter to the selector to switch the selector. Alarm information from the medical treatment device is then displayed on master display 130.

Having illustrated and described the principles of the invention in a preferred embodiment, it should be apparent to those skilled in the art that the preferred embodiment can be modified in arrangement and detail without departing from such principles.

For example, although the user input device 21 as shown in FIG. 1 is especially adapted for manipulating operation of the medical treatment device 12, the user input device 21 can also be used to change channels on the entertainment display 20. For example, the patient can manipulate the user input device 21 to direct the medical treatment device 12 to emit an infrared signal through the infrared emitter 24 to change the channel of the entertainment display 20 to whatever channel the patient wishes to view.

Further, although the entertainment display 20 is shown as a conventional television, the entertainment display 20 can alternatively be a computer display allowing the patient to be entertained by computer programs, such as computer games, word processing applications, spread sheets, browsers, or any other computer-related application programs during treatment. In such a case, the signal conductor 36 is connected to an input adapter on the computer display. Thus, the computer display is made operable to receive an interrupt whenever an alarm condition arises and to display the alarm information received through the signal conductor 36. For example, in "windows" applications, a new window can open on the computer display, without the patient taking any action.

Still further, although the entertainment display 20 is shown comprising a converter 48 for converting VGA signals to video signals, the medical treatment device 12 can be adapted to deliver video signals directly, rather than delivering VGA signals that require conversion to video. In such a case, the controller 42 delivers signals to the display adapter 46 and the display adapter 46 delivers the video signals to the entertainment display 20.

Although cables are shown to couple many of the components described herein, other means of communication can be used to couple the components, such as by infrared or radio signals.

In view of the many possible embodiments to which the principles of the present invention can be applied, it will be recognized that the illustrated embodiment is only a preferred embodiment of the invention and should not be taken as a limitation on the scope of the invention. Rather, the invention is defined by the following claims. We therefore claim as our invention all such embodiments that come within the scope of these claims.

What is claimed is:

1. An extracorporeal blood-treatment system, comprising:
    (a) a medical treatment device and an entertainment display operably connected to the medical treatment device so as to receive signals from the medical treatment device;
    (b) the medical treatment device being attached to a patient being operable to perform an extracorporeal treatment of the patient's blood;
    (c) the entertainment display being operable in a first mode to display entertainment images and in a second mode to display information related to the medical treatment device; and
    (d) the medical treatment device being operable to send signals to the entertainment display so as to cause the entertainment display to switch from the first mode to the second mode;
    (e) a user input device coupled to the medical treatment device that allows the patient to adjust treatment.

2. The system of claim 1, wherein the entertainment display is a television.

3. The system of claim 2, wherein, in the first mode of operation, the television is operable to receive radio-frequency signals corresponding to television programs displayed by the television and, in the second mode of operation, the television is operable to receive video signals corresponding to information from and pertaining to the medical treatment device.

4. The system of claim 2, wherein the medical treatment device comprises an infrared emitter operable to send a command to the entertainment display for switching the entertainment display from the first mode to the second mode, and the entertainment display comprises an infrared receiver operable to receive the command.

5. The system of claim 1, wherein the medical treatment device is a hemodialysis machine.

6. The system of claim 1, further comprising a user input device operably connected to the medical treatment device, the user input device being operable to permit a user to cause desired information concerning the medical treatment device to be displayed by the entertainment display whenever the entertainment display is in the second mode.

7. The system of claim 6, wherein the entertainment display, during operation in the second mode, displays a selector image, and the user input device is operable to allow user-manipulation of the selector image.

8. The system of claim 6, wherein the user input device further comprises a special-function key.

9. The system of claim 6, wherein the user input device is operable to allow a user to selectively control the medical treatment device whenever the entertainment display is in the second mode.

10. The system of claim 1, wherein the medical treatment device comprises a controller, a display adapter connected to the controller, and a converter connected to the display adapter.

11. The system of claim 10 wherein the converter is operable to receive signals from the display adapter and to convert the signals for transmission to the entertainment display.

12. An extracorporeal blood-treatment system, comprising:
   (a) treating means attached to a patient for treating blood extracorporeally routed from the patient for treatment and returned to the patient;
   (b) display means for entertaining the patient while the patient's blood is being extracorporeally treated by said treating means, said display means being operable in a first mode to display entertainment images and in a second mode to display information related to said treating means;
   (c) said treating means being operably connected to said display means such that said treating means can cause said display means to switch from the first mode to the second mode and to convey in the second mode information related to said treating means to said display means;
   (d) input means coupled to the treating means for adjusting treatment to the patient.

13. A medical system, comprising:
   a medical treatment device being attached to a patient and having a display adapter for medically treating the patient;
   the display adapter adapted for coupling to a display having a first mode of operation wherein a program unrelated to the medical treatment device is displayed and having a second mode of operation wherein information related to the medical treatment device is displayed; and
   a user input device coupled to the medical treatment device, the user input device adapted for allowing a user to use the display as a graphical user interface that is responsive to the user input device to selectively control the medical treatment device for adjusting treatment to the patient when the display is in the second mode of operation.

14. The medical system of claim 13 wherein the display is a television set.

15. The medical system of claim 14 wherein the first mode of operation includes receiving radio frequency signals to display television programs and the second mode of operation includes receiving video signals to display information related to the medical treatment device.

16. The medical system of claim 14 wherein the television set is adapted to display a selector image in the second mode of operation and the user input device is adapted to allow a user to move the selector image on the television set.

17. The medical system of claim 14 including an infrared emitter coupled to the medical treatment device and adapted to switch the television set from the first mode to the second mode of operation in response to an alarm condition.

18. The medical system of claim 13 wherein the medical treatment device is an extracorporeal blood processing device.

19. The medical system of claim 13 wherein the medical treatment device is adapted to be coupled to variable size displays.

20. A method for providing a person, watching an entertainment display, with information concerning a treatment alarm condition arising during an extracorporeal treatment of the person's blood being conducted while the person is watching the entertainment display, the method comprising the steps:
   (a) displaying on the entertainment display a program unrelated to the treatment;
   (b) when the treatment alarm condition arises, overriding display on the entertainment display of the program unrelated to the treatment with a display on the entertainment display of information related to the treatment; and
   (c) wherein step (b) occurs automatically without intervention by the person.

21. The method of claim 20, wherein, in step (b) during the alarm condition, the entertainment display displays a selector image.

22. The method of claim 21, including the step of providing a user input operable to move the selector image when the user input is manipulated during an alarm condition.

23. The method of claim 22, including the step of manipulating the user input to cause movement of the selector image so as to cause a change in the alarm-related information displayed on the entertainment display.

24. The method of claim 23, including the step of receiving control signals from the user input device for correcting the alarm condition.

25. The method of claim 22 wherein the alarm information includes a treatment parameter related to the alarm condition, the method further comprising the step of receiving a control signal from the user input and changing the treatment parameter in response to the control signal.

26. The method of claim 20, wherein step (a) comprises displaying on the entertainment display a television program.

27. A method of alerting a person to an alarm condition, arising with a medical device during a medical treatment performed using the medical device, through a display adapted to receive video signals and radio frequency (RF) signals, the method comprising the steps:
   (a) operating the display in a first mode in which the display receives and displays to the person images corresponding to the RF signals;
   (b) in response to the alarm condition, switching the display from the first mode to a second mode in which the display receives and displays to the person images corresponding to the video signals; and
   (c) wherein step (b) is performed automatically in response to the alarm condition without intervention by the person.

28. An extracorporeal blood-treatment system, comprising:

(a) at least two medical treatment devices for performing extracorporeal treatment on one or more patients;

(b) an input device for allowing the user to selectively control one or more of the medical treatment devices by using an entertainment display as a user interface that is responsive to the input device; and (c) a selector coupled between the input device and the medical treatment devices, the selector for routing signals from the input device to a selected medical treatment device for controlling the selected medical treatment device and for adjusting treatment to a patient in response to the input device.

29. The extracorporeal blood-treatment system of claim 28 including a master display coupled to the selector for receiving display signals from the selector and displaying information associated with the medical treatment devices on the display.

30. The extracorporeal blood-treating system of claim 29 wherein the master display automatically displays information associated with a medical treatment device when an alarm condition occurs on the medical treatment device.

31. A method for providing a person, watching an entertainment display, with information concerning a treatment alarm condition arising during an extracorporeal treatment of the person's blood being conducted while the person is watching the entertainment display, the method comprising the steps:

(a) displaying on the entertainment display a program unrelated to the treatment;

(b) when the treatment alarm condition arises, overriding display on the entertainment display of the program unrelated to the treatment with a display on the entertainment display of information related to the treatment; and (c) wherein in step (b) during the alarm condition, the entertainment display displays a selector image, and the user input is operable to move the selector image for adjusting treatment to a patient when the user input is manipulated during an alarm condition.

* * * * *